United States Patent
Yuan

(10) Patent No.: US 6,797,285 B1
(45) Date of Patent: Sep. 28, 2004

(54) LEAVES OF CAJANUS CAJAN(L.) MILLSP AND EXTRACT, FORMULATION AND USES THEREOF

(76) Inventor: Hao Yuan, Chinese Medicine Coxarthropathy Treatment Center of the Hospital Attached to Guangzhou Chinese Medicine University, No. 10, Airport Road, Guangzhou City, Guangdong Province (CN), 510405

( * ) Notice: Subject to any disclaimer, the term of this patent is extended or adjusted under 35 U.S.C. 154(b) by 73 days.

(21) Appl. No.: 10/018,981

(22) PCT Filed: Jun. 19, 2000

(86) PCT No.: PCT/CN00/00164
§ 371 (c)(1),
(2), (4) Date: Dec. 18, 2001

(87) PCT Pub. No.: WO00/78324
PCT Pub. Date: Dec. 28, 2000

(30) Foreign Application Priority Data

Jun. 18, 1999 (CN) .......................................... 99109147 A
Jul. 20, 1999 (CN) .......................................... 99109886 A

(51) Int. Cl.⁷ ............................. A61K 35/78; A61P 9/10
(52) U.S. Cl. ........................................ 424/725; 424/774
(58) Field of Search ......................................... 424/400

(56) References Cited

FOREIGN PATENT DOCUMENTS

| | | | |
|---|---|---|---|
| CN | 1174052 A | * 2/1998 | |
| CN | 1174052 | 2/1998 | .......... A61K/35/78 |

OTHER PUBLICATIONS

Liu Zhongqui et al., "Research for process of extracting the leaves of Cajanus cajan (l.) millsp in the shengmau chenggu tablet", Chinese Pharmacist–prepared Medicine, 1998, 20 (3), pp. 7–9.*

Liu zhongqui et al., "Research for Process of Extracting the Leavese of Cajanus Cajan(L.) Millsp in the Shengmai Chenggu Tablet", Chinese Pharmacist–prepared Medicine, 1998, 20(3), P7.

Sun Shamei et al., "Research for Pharmacology Action ) Formulation of Cajanin", Chinese Herbal Medicine, 1995, 26(3), p 147–148.

* cited by examiner

Primary Examiner—Thurman K. Page
Assistant Examiner—Simon J. Oh
(74) Attorney, Agent, or Firm—Fish & Richardson P.C.

(57) ABSTRACT

The invention discloses an extract of the leaves of *Cajanus Cajan*(L.) Millsp. and a process for the preparation of them. The invention also discloses the new uses of the leaves of *Cajanus Cajan*(L.)Millsp. and extract thereof, i.e. the uses for the preparation of medicaments for the treatment of ischemic necrosis of caput femoris and osteoporosis, for the improvement of hemorheological index, for anti-inflammatory and analgecization, for the enhancement of immunological function, and for the treatment of angina of coronary heart disease, fracture, cerebral infarction, bedsore, infected surface of wound and infected surface of wound of open fracture.

2 Claims, No Drawings

LEAVES OF CAJANUS CAJAN(L.) MILLSP AND EXTRACT, FORMULATION AND USES THEREOF

TECHNICAL FIELD

The invention relates to leaves of *Cajanus Cajan(L.)* Millsp. and extract, and pharmaceutical formulations thereof. The invention also relate to new uses of leaves of *Cajanus Cajan(L.)*Millsp. and extract, especially in pharmaceutical filed. The invention belongs to field of Chinese Traditional Medicine.

BACKGROUND OF THE INVENTION

*Cajanus Cajan(L.)*Millsp. is a subtropical bush plant, which belongs to adjonus genus of popilionaccae family, grows in south part of China, and also is called as Liudou, Niudou, Dourong or Liudian in Chinese. The plant has effects of clearing away heat and detoxicating, promoting blood circulation and relieving blood stasis, antisepsis, relieving inflammatory. Its root has effects of clearing away heat and detoxicating, stopping bleeding and relieving pain, and killing parasites. The tender leaves of it can be used in treating aphtha when chewed in mouth; the juice pressed from its tender leaves can be used in treating jaundice; the pulp obtained by pounding its tender leaves have the function of eliminating slough and promoting tissue regeneration on wound; the decoction of its leaves can be effective in cough and diarrhea. CN 11 74052A disclosed medical use of *Cajanus Cajan(L.)*Millsp., however, it is not clear to obtain active component of the plant because it was used in combination with other components and wasn't extracted. Therefor, its use is limited.

DESCRIPTION OF THE INVENTION

It is an object of the invention to provide an extract from leaves of *Cajanus Cajan(L.)*Millsp., so-called its active component.

It is a further object of this invention to provide a process for the preparation of such extract.

It is also a object of this invention to provide an pharmaceutical formulation comprising leaves of *Cajanus Cajan (L.)*Millsp. or its extract as active component.

It is another object of this invention to provide new use of leaves of *Cajanus Cajan(L.)*Millsp. or its extract, that is new use in the preparation of pharmaceutical formulations.

The extract of leaves of *Cajanus Cajan(L.)*Millsp. can be obtained as follows:

(1) The Purification and Preparation of Crude Materials
*Cajanus Cajan(L.)*Millsp.

[preparation] :The tender leaves and branches of *Cajanus Cajan(L.)*Millsp. is collected, removed impurity and old branches, cleaned and dried in the shade. They are cut into about 5 cm small parts and put in clean container for later use.

(2) Extraction, Concentrating and Drying of Drugs

These treated *Cajanus Cajan(L.)*Millsp. are put in multi-function extractor. Water is added in 10-fold amount of drugs, and then these drugs are immersed for about 0.5 to 2 hours. The mixture is decocted 14 times for 1–2 hours each times. After filtered, the filtrates is drew immediately into a vacuum concentrator(atmospheric pressure is −0.08 Mpa and temperature is 60° C.) and concentrated to relative density of 1.05–1.15 (detected at 60° C.). After filtered with 80 mush filter cloth, the filtrates is filtered by continuous centrifugation, and then the centrifugal fluid is dried by spray-drying process to obtain dried extract powder, that is the active component extract according to the invention which is put in clean and air-tight container.

In order to produce extract according to the invention, the preferable process includes the following steps. These treated *Cajanus Cajan(L.)*Millsp. are put in multi-function extractor. After water is added in 10-fold amount of drugs and these drugs are immersed for about 1 hour, the mixture is decocted 3 times for 1.5 hours each times. After filtered, the filtrates is drew immediately into a vacuum concentrator and concentrated under the condition of −0.08 Mpa and 60° C. to relative density of 1.05–1.15 (detected at 60° C.). After filtered with 80 mush filter clothes, the filtrates is filtered by continuous centrifugation at 15,000 r.p.m with the flow amount of 50L/hour, and then the centrifugal fluid is dried by spray-drying process under the condition of 180° C. at entrance, 4 seconds of dried time and 80° C. at exit. The resultant dried extract powder is put in clean and air-tight container.

The extract of leaves of *Cajanus Cajan(L.)*Millsp. can be formulated into pharmaceutical formulations for clinic use such as tablets, pills, powders, capsules, oral liquids and so on by standard methods, in which the extract is present as active component at effective therapeutic amount, in generally range from 0.01 to 99.9%, preferably, 1 to 90%, more preferably from 5 to 80%, most preferably from 10 to 70%. Alternatively, dried leaves of *Cajanus Cajan(L.)*Millsp. can be ground to powder as active component to formulated into clinic pharmaceutical formulations by standard methods.

The capsule of leaves of *Cajanus Cajan(L.)*Millsp. can be produced by mixing the extract optionally with excipient such as starch and filling into capsule. It is confirmed by tests that leaves of *Cajanus Cajan(L.)*Millsp. or extract thereof have the following novel medical uses.

1. The Use of Leaves of *Cajanus Cajan(L.)*Millsp. or Extract Thereof for Manufacture of a Medicament for the Treatment of Osteoporosis In order to observe the effect of the capsule of leaves of *Cajanus Cajan(L.)*Millsp on experimental osteoporosis, the osteoporosis model is made by tretinoin. The result indicated that the capsule notably increased levels of calcium and phosphorus in serum, decreased the level of alkaline phosphatase, and enhanced BMC and BMD in rats. From the observation on pathological section, it is showed that the capsule significantly improved the quality of bone trabecula, reduced the numbers of osteoclast and promoted the growth of osteoblast and thereby prevented and treated osteoporosis.

2. The Use of Leaves of *Cajanus Cajan(L.)*Millsp. or Extract Thereof for Manufacture of a Medicament for the Treatment of Ischemic Necrosis of Caput Femoris After established the New Zealand rabbit model of ischemic necrosis of caput femoris by horse serum-hormone, the capsule at high, middle and low dosages was administrated to the animals separately, normal control group and model control group were set simultaneously. The result showed that the capsule had notable effect on treatment of hormone-induced ischemic necrosis of caput femoris after detecting the density of bone tissue in proximal end of femur, observing by magnifying X-ray photo, pathologic examination by light microscope, observing under television microscope and dynamic measurement for metabolism of bone tissue.

3. The Effect of Leaves of *Cajanus Cajan(L.)*Millsp. or Extract Thereof on the Improvement of Hemorrheology The test of microcirculation in rat mesentery demonstrated that the capsule can significantly increase velocity of blood flow, infinitesimal calculus of velocity and state of blood flow. The index of hemorrheology for rat acute hypostasis model displayed that the capsule can enhance the specific viscosity of total blood and plasma and decrease blood sedimentation.

4. The Use of Leaves of *Cajanus Cajan(L.)*Millsp. or Extract Thereof for Manufacture of a Medicament for Anti-inflammatory and Analagecization The tests of dimethylbenzene induced inflammation on mice pinna and cotton ball granuloma on mice showed that the capsule can alleviated notably ear tumefaction reduced by dimethylbenzene and cotton ball granuloma. Tests of torsion method and hot plate method on mice showed that the capsule declined clearly the number of torsion mice, prolonged the period of the first torsion, increased percent of analgesis, and increased threshold value of pain on mice.

5. The Use of Leaves of *Cajanus Cajan(L.)*Millsp. or Extract Thereof for Manufacture of a Medicament for Enhancement of Immune Function Mice were induced by prednisone acetate to low immune function. In these models, the capsule according to the invention not only have the trend of enhancing phagocytic function of mononuclear leukocyte in mice, but also increased markedly the weight of immune organs such as thymus, spleen and the level of hemolysin in mice in which chicken red blood cell acts as immunogen. In addition, It significantly increased the present rate of transition state T-lymphoblastoid cell and the rate of transformation of lymphocyte stimulated by phytohematoagglutinin in mice.

6. The Use of Leaves of *Cajanus Cajan(L.)*Millsp or Extract Thereof for Manufacture of a Medicament for the Treatment of Bed Sore It can be seen by clinical observation that the curative effect of leaves of *Cajanus Cajan(L.)*Millsp. and extract thereof are superior to that of traditional ointment for promoting muscle growth on treatment of bed sore. The leaves of *Cajanus Cajan(L.)*Millsp. and extract thereof can not only shorten course of treatment, but also decrease the scar after healing.

7. The Use of Leaves of *Cajanus Cajan(L.)*Millsp. or Extract Thereof for Manufacture of a Medicament for the Treatment of Infected Wound The leaves of *Cajanus Cajan(L.)*Millsp. and extract thereof have effects of promoting the growth of epithelium granulation tissue on surface of wound, increasing supply of blood to surface of wound, speeding up wound healing, decreasing growth of scar tissue, and enhancing the quality of healing. As far as anti-infectious effect is concerned, it can be found that leaves of *Cajanus Cajan(L.)*Millsp. and extract thereof have good effect against infection on infected wound, which is manifested by quickly disappear of wound and inflammatory reaction, especially by decreasing rapidly the exudation on surface of wound after administration and clean surface of wound, it is implied that the medication has good effect on resisting inflammatory exudation.

8. The Use of Leaves of *Cajanus Cajan(L.)*Millsp. or Extract Thereof for Manufacture of a Medicament for the Treatment of Infected Wound of Open Fracture The leaves of *Cajanus Cajan(L.)*Millsp. and extract thereof have good effect of anti-infection in clinical test and can promote the growth of granulation tissue, increase the supply blood for wound surface, enhance the healing of wound surface, particularly the growth of granulation tissue, as called "granulation island of bone", on the bone surface exposed to wound surface.

The results of clinical treatment also showed that the leaves of *Cajanus Cajan(L.)*Millsp. and extract thereof have good curative effect on angina pectoris of coronary heart disease, cerebral infraction, and fracture.

In order to understand the essence of the invention further, the process of producing the extract of *Cajanus Cajan(L.)* Millsp., the pharmacological study of leaves of *Cajanus Cajan(L.)*Millsp. and extract thereof as well as the results of study will be described in detail by means of the following examples so as to illustrate the novel uses in pharmaceutical field.

THE BEST EMBODIMENT OF THE INVENTION

EXAMPLE 1

Process of Producing Extract from Leaves of *Cajanus Cajan(L.)*Millsp and the Capsule Thereof 10 kg crude leaves of *Cajanus Cajan(L.)*Millsp. was weighted from same batch and cut to sections. Water was added in amount of 10 fold and heated to decoct 3 times, 1.5 hours each times. After filtration, these filtrates are combined and concentrated in vacuum to relative density 1.5 under −0.08 Mpa and 60° C. precipitation was removed away by centrifugation (15000 r.p.m), and the resulting filtrate was dried to yield extract powder (0.81 kg) by spray drying process. The obtained extract powder was laid in clean and air tight container for later use.

The dried extract powder of leaves of *Cajanus Cajan(L.)* Millsp. as above was filled into pharmaceutical capsule to obtain capsule preparation, which will be called as Shengmaichenggu Capsule (Pulse-facilitation and bone-formation Capsule) in next context.

EXPERIMENTAL EXAMPLE 2

The Pharmacological Effect of Preparations of Leaves of *Cajanus Cajan(L.)*Millsp. on Treating Osteoporosis 1. Test of Pathologic Change in Bone Induced by Tietinoin
  Materials
  Medicaments: Capsule of Shengmaichenggu Capsule (Pulse-facilitation and bone-formation Capsule); tretinoin, produced by the 6th pharmaceutical factory of SHANGHAI, Number of batch: 960322; Powder of LONGMU ZHUANGGU, produced by JIALNMIN pharmaceutical factory of WUHAN, Number of batch: 960111.

Animals: 100 male SD rats, supplied by the animal feedlot of the health department of guangdong province, body weight: 250–300 g; certificate number: 96A02

Feeds: Standard feeds provided by the animal feedlot of the health department of guangdong province.

Equipment: KANGNING type of US: 55 automatic biochemical analyzer, TECHNICON, RA2000, DEXA (HologicQDR-2000 operators Manual) from US.

Regents: TRACE from Australia (sell from Longmarch company of SHANGHAI)

Methods and Results

Animals were randomly divided into six groups which include control group, model group, LONGMU ZHUANGGU-group, Shengmaichenggu Capsule-group in three dosages (the dosage is respectively 7.68 g/kg/day, 3.84 g/kg/day, 1.92 g/kg/day and the amount of crude drugs used in clinic was 1 g/kg/day). After model group, LONGMU ZHUANGGU-group and three Shengmaichenggu Capsule-group were administrated with tretinoin 70 mg/kg/day simultaneously and medicaments for 2 weeks by filling into stomach, the administration of tretinoin was stopped. The LONGMU ZHUANGGU-group and the three Shengmaichenggu Capsule-group were continuously administered for 5 weeks. Distilled water was administered in 20 ml/kg/day for control group and model group. Each item was tested as follow.

(1) Contents of Calcium, Phosphorus, and Alkaline Phosphatase(AKP) in Serum 5 ml blood were taken from eyeball of rats in the morning. The contents of calcium, phosphorus, and alkaline phosphatase in serum were determined by 550 automatic biochemical analyzer, TECHNICON, RA2000 of US with TRACE of Australia. The result was listed in following table 1.

As shown by the result, The content of phosphorus in serum of model group dropped significantly ($p<0.001$) compared with that of control group. The contents of calcium and phosphorus of the three Shengmaichenggu Capsule-group at high, middle and low dosage increased notably ($p<0.001$, $p<0.01$, or $p<0.05$) compared with that of model group. The content of alkaline phosphatase in serum of Shengmaichenggu Capsule-group at low dosage decreased significantly ($p<0.05$) compared with that of model group.

(2) The Bone Area (AREA), Bone Mineral Density (BMD), Bone Mineral Content (BMC) Tested by Double Photon Bone Density Assay The AREA, BMD, and BMC of rats were determined by DEXA (Hologic QDR-2000 operators Manual) under anesthesia by pentobarbital sodium. The AREA, BMD, and BMC of rats were determined at point of global (whole rat), R1 (left head of femur), R2 (right head of femur), R3 (right femur), R4 (left femur), R5 (lumbar vertebra), and NETAVG (the sum of R1, R2, R3, R4, R5) (the result was showed in table 2 and 3).

TABLE 1 the effect of capsule of SHENGMAI CHENGU on contents of calcium, phosphorus, and alkaline phosphatase in serum (x ± s)

| Group | Numbers of animal | Dose (kg/day) | P | Ca | AKP |
|---|---|---|---|---|---|
| Control group | 6 | 20 ml distilled water | 2.53 ± 0.12 | 2.15 ± 0.29 | 329.17 ± 32.30 |
| Model group | 8 | 20 ml distilled water | 2.13 ± 0.20*** | 1.91 ± 0.35 | 334.38 ± 97.63 |
| LONGMU ZHUANGGU-group | 8 | 5 g | 2.49 ± 0.19### | 2.14 ± 0.17 | 341.75 ± 37.48 |
| Shengmaichenggu Capsule-group | 8 | 7.68 g | 2.48 ± 0.15### | 2.24 ± 0.22# | 319.13 ± 49.43 |
| Shengmaichenggu Capsule-group | 8 | 3.84 g | 2.45 ± 0.12### | 2.29 ± 0.24## | 282.13 ± 26.22 |
| Shengmaichenggu Capsule-group | 8 | 1.92 g | 2.42 ± 0.11### | 2.56 ± 0.36### | 304.15 ± 64.72# |

Note: *P < 0.05, **P < 0.01, #P < 0.05, ##P < 0.01
*P < 0.05 when model group is compared with control group, P < 0.01 when model group is compared with control group, *P < 0.001 when model group is compared with control group.
P < 0.05 when positive medicament group or Shengmaichenggu Capsule-group is compared with model group. ##P < 0.01 when positive medicament group or Shengmaichenggu Capsule-group is compared with model group. ###P < 0.001 when positive medicaments group or Shengmaichenggu Capsule-group is compared with model group.
The indication of signals in the following tables is same as that in Table 1 except annotation otherwise.

TABLES 2

The effected of Shengmaichenggu Capsule-group on AREA, BMD, and BMC in Globan rats.

| Group | Number of animal | Dosage (kg/day) | Global Area | Global BMC | Global BMD |
|---|---|---|---|---|---|
| Control group | 5 | 20 ml distilled water | 56.4128 ± 5.1772 | 6.5012 ± 0.6180 | 0.11526 ± 0.00356 |
| Model group | 5 | 20 ml distilled water | 48.2582 ± 6.2002** | 5.0524 ± 0.7169*** | 0.10468 ± 0.00586** |
| Shengmaichenggu Capsule-group | 5 | 5 g | 55.2327 ± 3.4262# | 6.2946 ± 0.6982## | 0.11372 ± 0.00568### |
| Shengmaichenggu Capsule-group | 5 | 7.68 g | 54.1496 ± 3.7743# | 6.0855 ± 0.6068# | 0.11228 ± 0.00490# |
| Shengmaichenggu Capsule-group | 5 | 3.84 g | 58.5560 ± 2.6876### | 6.6388 ± 0.2893### | 0.11342 ± 0.00393## |
| Shengmaichenggu Capsule-group | 5 | 1.92 g | 49.9117 ± 4.0395 | 5.5338 ± 0.6037 | 0.11072 ± 0.00516 |

| Group | Number of animal | Dosage (kg/day) | R5 Area | R5 BMC | R5 BMD |
|---|---|---|---|---|---|
| Control group | 5 | 20 ml distilled water | 2.70206 ± 0.7308 | 0.3693 ± 0.1073 | 0.13592 ± 0.00383 |
| Model group | 5 | 20 ml distilled water | 2.7089 ± 0.2626 | 0.3112 ± 0.0522 | 0.11454 ± 0.013** |
| Shengmaichenggu Capsule-group | 5 | 5 g | 3.01614 ± 0.6008 | 0.3878 ± 0.1189 | 0.12664 ± 0.0136 |
| Shengmaichenggu Capsule-group | 5 | 7.68 g | 3.02076 ± 0.1870 | 0.3958 ± 0.365 | 0.13082 ± 0.00456# |
| Shengmaichenggu Capsule-group | 5 | 3.84 g | 3.032323 ± 0.3288 | 0.3995 ± 0.00269 | 0.13224 ± 0.00643# |

TABLES 2-continued

The effected of Shengmaichenggu Capsule-group on AREA, BMD, and BMC in Globan rats.

| | | | | | |
|---|---|---|---|---|---|
| Shengmaichenggu Capsule-group | 5 | 1.92 g | 2.77596 ± 0.5044 | 0.3567 ± 0.0692 | 0.12866 ± 0.0141# |

As shown by the results, AREA, BMC and BMD of Global in model groups remarkably dropped ($P<0.001$, $P<0.01$ or $P<0.05$) compared with that of control group. Whereas AREA, BMC and BMD of Global in Shengmaichenggu Capsule-group at high, middle dosage remarkably increased ($P<0.001$, $P<0.01$ or $P<0.05$) compared with that of model group. BMD of R5 in model group remarkably reduced ($P<0.01$) compared with control group, BMD of R5 in Shengmaichenggu Capsule-group increased significantly ($P<0.05$) compared with model group, BMC and AREA of Shengmaichenggu Capsule-group have the trend of increasing compared with model group.

ously. Osteoblast increased as compared with that of model group, the increase of osteoblast is not obviously.

Shengmaichenggu Capsule-group at high dosage: The structure of bone trabecula was normal and regular, didn't become slender and smaller; hematopoietic cell was abundant; osteoblast increased, osteoblast reduced.

Shengmaichenggu Capsule-group at middle dosage: The structure of bone trabecula was almost normal and regular, didn't become slender and smaller; hematopoietic cell was relative abundant; Medullary cavity enlarged didn't enlarged obviously; osteoblast increased, the increase of osteoblast is not obvious.

TABLE 3

The effects of Shengmaichenggu Capsule-group on NETAVG AREA, BMC, BMD, in rats

| | | | NETAVG | | |
|---|---|---|---|---|---|
| Group | Case | Dosage (kg/day) | Area | BMC | BMD |
| Control group | 5 | 20 ml distilled water | 5.1039 ± 0.9459 | 0.6701 ± 0.1478 | 0.13056 ± 0.00563 |
| Model group | 5 | 20 ml distilled water | 5.0508 ± 0.3066 | 0.5656 ± 0.0647 | 0.11190 ± 0.01000** |
| Shengmaichenggu Capsule-group | 5 | 5 g | 5.3048 ± 0.9553 | 0.6645 ± 0.1997 | 0.12322 ± 0.01490 |
| Shengmaichenggu Capsule-group | 5 | 7.68 g | 5.5173 ± 0.2050# | 0.6858 ± 0.0563 | 0.12416 ± 0.00626# |
| Shengmaichenggu Capsule-group | 5 | 3.84 g | 5.5819 ± 0.4001 | 0.7006 ± 0.0647 | 0.12546 ± 0.00542# |
| Shengmaichenggu Capsule-group | 5 | 1.92 g | 5.2240 ± 0.6167 | 0.6369 ± 0.0854 | 0.12156 ± 0.01010 |

As shown in results, the BMD of NETAVG in model group decreased markedly ($P<0.0$)compared with that of control group, the BMD of Shengmaichenggu Capsule-group at high and middle dosage increased markedly ($P<0.05$) compared with that of model group BMC and AREA of Shengmaichenggu Capsule-group have the trend of increasing compared with that of model group.

(3) Examination of Histomorphology

Method

The head of Femur was cut along coronal section of the head of femur and cross section of midpiece of femur, fixed with 10% formalin buffer and washed with running water after decalcification with 5% nitric acid. After imbed with paraffin, it was cut and stained with HE. Bone trabecula, osteoblast and osteoclast in HE section of bone were observed to see whether any changes occur.

Results

Normal control group: regular and compact bone trabecula without fragmentation were observed.

Model group: bone trabecala became slender and smaller with fragmentation, the structure became disorder, even disappear. Hematopoietic cell reduced obviously. Medullary cavity enlarged; osteoblast decreased obviously, and osteoclast increased obviously.

LONGMU ZHANGGU Group: The structure of bone trabecula was irregular, but it didn't become slender obvi- Shengmnichenggu Capsule-group at low dosage Group: The structure of bone trabecula was almost normal and regular, didn't become slender, osteoblast increased slightly, the increase of osteoblast is not obvious.

Summary:

The above experiments discussed the prophylaxis and treatment effects of Shengmaichenggu Capsule on osteoporosis induced by tretinoin. The result showed that Shengmaichenggu Capsule can raise the contents of calcium and phosphorus in blood serum, promoted the growth of osteoblast, improved the quality of bone trabecula, increased bone mineral content and bone mineral density. These indicated that the medicament of the invention have the effect of reinforcing vital energy and strengthening bone to prevent the occurrence of osteoporosis.

2. Clinical Observation of the Effect of Capsule of Leaves of Cajanus Cajan(L.)Millsp. on Treating Osteoporosis.

Clinic Information 200 patients were chosen, in which there were 78 male and 122 female. 9 patients were 45–50 year old. 28 patients were 51–60 year old. 122 patients were 61–70 year old. 34 patients were 71–80 year old. 7 patients were 81–99 year old. Their average age was 65 year old. Their chief complaints included spontaneous ostealgia which occurred continually or occasionally in different degree. The patients usually had backache or pain in hip and knee joint, felt aching and weak in loin and knee. When tired, the above symptoms became heavier. The patients can not sit for a long time and were easy to be fatigue. Their activity was hindered and restricted. Even someone often need taking analgesic in order to relieve their pain, but the effect is not satisfied or the pain recurred after stopping administration. Their courses of treatment were within 3 months to 3.5 years and average course was 9 months. By physic examination, it was found that 127 patients had hump back or deformity of kyphosis in varying degree, 132 cases were accompanied with tenderness and percussion pain on vertebrae, percussion pain on hip and knee joint. By examination with X-ray, it was found that there were 112 cases with spinal compression fracture, 15 cases with hip fracture, 27 cases with wrist fracture, 5 cases with arm fracture, 6 cases with multiple fracture. All patients showed obvious symptom of osteoporosis such as low bone density, thin cortex of bone, slender and sparse bone trabecula without other possibility of pathologic fracture such as other disease or metastatic carcinoma.

Method of Treatment (1) General therapy: those who had slight compression fracture or center depressed compression fracture on spine needn't lie in bed. Those whose vertebral body was compressed about $\leq 1/3$ need lie in bed for two weeks. Those whose vertebral body was compressed about $\geq 1/2$ or many vertebral body was compressed to be deformed and had bad stability need lie in bed for 3–5 weeks. All of the patients need small pillows under the center of injured vertebrae so as to relieve deformity of ithycyphos in late time. Those who had hip fracture need therapy of bone traction or fixing with screw nail. Be careful to prevent from bed sore and infection in lung and urinary system during time of lying in bed.

(2) Treatment with Shengmaichenggu Capsule by Oral Administration (3) Accessory Therapy Patients are encouraged to maintain activity outdoor during middle and later period in order to increase bone stress stimulation, enhance the bone firm and tenacious so as to make bone strong and make joints agile. Don't let the patients do excising violently and carry heavy goods. Those who had fracture should combine other therapies, for example, infrared radiation, TDP lamp irradiation and fumigation with traditional Chinese medicine in order to promote healthy.

Treatment Result (1) Standard of Evaluating Curative Effect

Notable effect: It means that all clinical symptoms disappeared, normal activity functions were obtained, fracture was healed, or compress-deformed vertebral body recovered partly, and symptoms of osteoporosis are improved.

Improved effect: A majority of clinical symptoms disappeared, fracture healed or heal was delayed, compression of vertebral body didn't become serious, symptoms of osteoporosis are improved or changed unclearly, daily activity can be restored; or main clinical symptoms disappeared, activity function improved obviously.

Invalid: Main clinical symptoms, physical signs such as bone pain symptom, activity function and osteoporosis all were not improved or became serious.

(2) Results of Curative Effect

According to above standard of evaluating curative effect, results was that there were 89 cases with notable effect, 29 cases with improved effect and total improved effect rate was 85.5% after 2–5 month treatment. 63 of the patients were visited during 3–5 years, and non of them has fracture again and their body condition recovered very well. 38 patients who had suffered vertebral body compress fracture have restored the ability of labour.

EXPERIMENTAL EXAMPLE 3

Observation on Effect of the Capsule of Leaves of *Cajanus Cajan*(*L*.) Millsp. on Angina Pectoris of Coronary Heart Disease 1. Clinical Information 45 patients were treated, in which 30 patients were male and 15 patients were female. Among them, the oldest patient was 75 years old, the youngest patient was 38 years old and average ages was 54 years old; The shortest course of treatment was 1 month, the longest course of treatment was 10 years and average course was 38 months.

According to the diagnose standard of coronary heart disease made by WHO in 1981 and the standard of naming and diagnosing coronary heart disease made by experts group of coronary heart diseases in the first national conference of internal medicine in 1980, 37 patients who had suffered from exertional angina pectoris was diagnosed in different degree which include 5 patients as degree I, 16 patients as degree II, 10 patients as degree III and 6 patients as degree IV. 8 patients had suffered from spontaneous angina pectoris, among them 16 patients also suffered from kinds of arrhythmia.

2. Method of Treatment

All patients were treated with Shengmaichenggu Capsule and their electrocardiogram were checked before and after treatment.

3. Standard of Curative Effect and Treatment Results (1) Standard of Curative Effect The standard of curative effect on angina pectoris of coronary heart disease revised by national symposium on preventing and treating angina pectoris of coronary heart disease and arrhythmia by methods of traditional Chinese medicine and Western medicine on September, 1979 is incorporated as reference here.

(2) Treatment Results

The effect on angina pectoris symptom: there were 29 cases with notable effect, 15 cases with improved effect and 1 case with invalid effect; The effect on electrocardiogram: there were 13 cases with notable effect, 16 cases with improved effect and 16 cases with invalid effect. As far as accompanied symptom of arrhythmia, majority of patients had disappeared or reduced obviously.

EXPERIMENTAL EXAMPLE 4

The Effect of Capsule of Leaves of *Cajanus Cajan* (*L*.) Millsp on Treating Cerebral Infarction 1. General Information 60 patients were chosen who conformed to the standard of diagnose and evaluation of curative effect on apoplexy according to traditional Chinese medical science and were diagnosed by CT examination. They were divided into two groups in which there were 32 patients in treated group including 23 male patients and 9 female patients. Their ages were from 53 to 78 years old and their average age was 64.8 years old. The course of treatment was from 3 days to 1 month. There was 28 patients in control group including 22 male patients and 6 female patient, whose ages was from 54 to 72 years old, and the average ages was 61.3 years old. The course was from 2 to 7 months.

2. Method of Treatment

All patients were treated with SHENGMAICHENGGU capsule. The dosage is that three times every day, 4 capsules one time, and three months is one course. Patients in control group were treated with compound DANSHEN tablets three times one day, three tablets once. All patients were treated for six months. Physiotherapy, acupuncture and moxibustion therapy was used during recovering period.

3. Observation of Curative Effect (1) Standard of Curative Effect substantially cured: It means that myodynamia increased more than two degrees, physical sign of nervous system substantially disappeared, and patient could care oneself.

Notable effect: It means that myodynamia increased 1–2 degrees and patient couldn't care oneself.

Invalid effect: It means that myodynamia increased up to one degrees.

(2) Treatment Results

In treated group, there were 14 cases substantially cured (43.75%), 13 cases with notable effect (40.63%), 2 cases with effect (6.25%), 3 cases with invalid effect (9.37%), the total effective rate is 90.63%. In the control group, 8 cases substantially cured (28.57%), 11 cases with notable effect (39.29%), 4 cases with effect (14.28%), 5 cases with invalid effect (17.86%), the total effective rate is 82.14%. There is a significant difference between the two groups(t=3.425, p<0.01).

EXPERIMENTAL EXAMPLE 5

Clinical Observation on the Effect of Treating Fracture by the Capsule Made from the Leaves of *Cajanus cajan*

1. Clinical Information (1) Selected 108 cases suffered from fresh closed limb fracture, in which 60 are male and 48 female, varying in age from 18 to 79 years old, with an average age of 40.8 years old, wherein there were 11 cases with humerus fracture, 30 cases with ulnar fracture, 14 cases with metacarpal fracture, 17 cases with femur fracture, 21 cases with peroneotibial fracture, 15 cases with metatarsophalangeal fracture. The cases were divided into two groups according to the sequence of seeking medical advice. The group with odd numbers was treated group, and that with even numbers was control group. There are 54 cases in each group. The two groups are comparable with substantially similar distribution of age, sex and fracture part (p>0.05) (See table 4–6).

TABLE 4

Age distribution of the two groups

| Age (years) | Treated group Cases (%) | Control group Cases (%) | Total Cases (%) |
| --- | --- | --- | --- |
| 18–30 | 16(29.63) | 17(31.43) | 33(30.56) |
| 31–40 | 7(12.96) | 8(14.81) | 15(13.89) |
| 41–50 | 9(16.67) | 7(12.96) | 16(14.81) |
| 51–60 | 10(18.52) | 9(16.67) | 19(17.59) |
| 61–78 | 12(22.22) | 13(24.07) | 25(23.15) |

TABLE 5

Sex distribution of the two groups

| Sex | Treated group Cases (%) | Control group Cases (%) | Total Cases (%) |
| --- | --- | --- | --- |
| Male | 32(59.26) | 28(51.85) | 60(55.56) |
| Female | 22(40.74) | 26(48.15) | 48(44.44) |

TABLE 6

Fracture part distribution of the two groups

| Fracture part | Treated group Cases (%) | Control group Cases (%) | Total Cases (%) |
| --- | --- | --- | --- |
| Humerus | 5(9.26) | 6(11.11) | 11(10.19) |
| Ulnoradial bone | 16(29.63) | 14(25.93) | 30(27.78) |
| Metacarpophalangeal bone | 8(14.81) | 6(11.11) | 14(12.96) |
| Femur | 9(16.67) | 8(14.81) | 17(15.74) |
| Peroneotibial bone | 9(16.67) | 12(22.22) | 21(19.44) |
| Metatarsophalangeal bone | 7(12.96) | 8(14.81) | 15(13.89) |

(2) Method of Treatment

The patients of two groups were treated with conventional method of reduction, fixation and function training. Additionally, patients of the treated group took the capsule made from the leaves of *Cajanus cajan* orally, 4 pills each time, thrice a day. One treatment-course consisted of 15 days. The capsule was administered continually for 1–3 course or even longer according to the patients' condition. The patients of the control group took SANQI (one Chinese herbal medicine) capsule orally, 4 pills each time, thrice a day. One treatment-course consisted of 15 days.

(3) Standard of Curative Effect: Evaluating the Curative Effect According to the Fracture Healing Time.

Cure: To reach the clinical healing standard ahead of at least ⅓ period as compared with the time needed for the same type of fracture without the treatment of the invention.

Notable effect: Reach the clinical healing standard ahead of at least ¼ period as compared with that for the same type of fracture without the treatment of the invention.

Effect: Reach the clinical healing standard ahead of at least ⅕ period as compared with that for the same type of fracture without the treatment of the invention. Invalid effect: With the same healing period as that for the same type of fracture without the treatment of the invention.

The clinical healing standard and the healing time for fracture took reference to Tong's standards, et al. To evaluate the functional recovery according to Yang's evaluating standard.

Excellent: The fracture is healing. The articulations' moving range is formal or nearly formal. Recover to work;

Good: The fracture is healing. The articulations' move range is more than 30°. The patient can take care of oneself in daily life.

Bad: The fracture is healing. The articulation moves with obvious difficulty. The forearms can not rotate freely or can not hold heavy objects. The patients have pain at articulations of lower limbs or can not walk with heavy load.

(4) Treatment Results:

The cases of each groups underwent 1–3 courses. Comparison of the fracture healing time is shown in table 7. The data were statistically analyzed with $X^2$-test. The comparison of the total effective rate between two groups showed no significant difference (P>0.05). But one control case belonged to the bad grade. The excellent-good rate of the control group was slightly lower than that of the treated group.

TABLE 7

Comparison of the fracture healing time between two groups (day)

| Group | Cure | Notable effect | Effect | Invalid effect | Effective rate (%) |
|---|---|---|---|---|---|
| Treated | 27 | 15 | 9 | 3 | 94.44 |
| Control | 69 | 10 | 2 | 9 | 46.30 |

TABLE 8

Comparison of the function recovery between two groups

| Group | Excellent | Good | Fair | Bad | Excellent-good rate (%) |
|---|---|---|---|---|---|
| Treated | 47 | 6 | 1 | 0 | 98.15 |
| Control | 44 | 8 | 1 | 1 | 96.30 |

EXPERIMENTAL EXAMPLE 6

Pharmacodynamic Experiment of the Curative Effect of the Capsule Made from the Leaf of *Cajanus cajan* on Treating Ischemic Necrosis of Caput Femoris 1. Object: To evaluate the pharmacodynamic effect of Shengraichenggu Capsule (Pulse-facilitation and bone-formation Capsule) on treating hormone-induced ischemic necrosis of caput femoris.

2. Method: A model of ischemic necrosis of caput femoris of the invention was made on New Zealand rabbits induced by horse blood sera plus hormone. The establishment of the model was identified after 5 months. Then the model rabbits were administered Shengmaichenggu Capsule (Pulse-facilitation and bone-formation Capsule) at higher, middle and lower dosages respectively. Normal control and model control groups were set up at the same time. The animals were killed 8 weeks after the administration. The therapy effect was evaluated by the examination of amplified X-ray photo, bone density, optical microscope, electron microscope, bone metabolic dynamics et al.

3. Results: (1) Horse blood sera plus hormone can produce a typical model of ischemic necrosis of caput femoris; (2) Pharmacodynamic experiment indicated that: (i) The amplified X-rays picture showed that the conformation of Shengmaichenggu Capsule-treated groups at higher and middle dosage were nearly normal. For the model group, the bone density of proximal thighbone was not even. It showed a necrosis appearance; (ii) It could be seen under an optical microscope that the bone cavity rate in the caput femoris decreased for every dosage groups, meanwhile the counting numbers of both blood vessels and osteoblasts increased. There was a significant difference as compared with the model group ($P<0.05$); (iii) It could be seen under an electron microscope that there had an abundance of functional organelles in the osteoblasts for every dosage groups, and the bone cells were mainly in osteoblastic phase and resorptional phase; (iv) The bone density of proximal thighbone of lower dosage group was higher than that of other groups, and there was a significant difference as compared with the model group and the normal control group ($P<0.05$). (v) The bone metabolic dynamics: The bone growth values of higher and lower dosage groups increased significantly as compared with that of the model group ($P<0.05$); (vi) Blood biochemistry indexes: The level of total cholesterol and triglyceride in serum had no significant difference among these groups.

4. Conclusion: Shengmaichenggu Capsule (Pulse-facilitation and bone-formation Capsule) has significant effect on treating hormone-induced ischemic necrosis of caput femoris. The main mechanism is promoting the restoration and regeneration of blood vessels in bony tissue and marrow, and promoting the growth of new bone.

EXPERIMENTAL EXAMPLE 7

Test of the Effect of the Capsule Made from the Leaves of *Cajanus cajan* on Optimizing Hermorheology Index of Rat Acute Blood Stasis Model 1. Experimental Materials Medicaments: Shengmaichenggu Capsule (Pulse-facilitation and bone-formation Capsule); Epinephrine hydrochloride injection 1 mg/ml, supplied by Min Sheng pharmaceutical manufactory, Hangzhou, lot number: 951012; Tetramethylpyrazine phosphate, supplied by Shi Qiao pharmaceutical manufactory, Guangzhou, lot number: 950116; Pentobarbital sodium, lot number: 950202.

Animals: 60 male SD rats, body weight 150–200 g, supplied by the animal feedlot of the Health Department of Guangdong Province. Certificate number: 96A02.

2. Method and Results

The rats were divided into 6 groups randomly, i.e. normal control group, blood stasis model group, Tetramethylpyrazine phosphate-treated group and three Shengmaichegngu capsule-treated groups (the dosage were shown in table 9). The control group and the blood stasis model group were administered equal volume of distilled water by gavage. Every treated groups were administered liquor drug with different concentrations at a dosage of 2 ml/100 g weight/day, once daily at a fixed time for 20 days. When 24 hours after the last administration, animals except the normal control group were injected epinephrine hydrochloride hypodermically for two times (0.8 mg/kg) with an interval of 3 hours. The rats were immersed in water at $4\pm1°$ C. for 5 minutes at the time of 1.5 hour after the first injection of epinephrine hydrochloride, then the animals fast. In the next morning, eyeball blood was taken from anesthetized animals (injected pentobarbital sodium to abdominal cavity at a dosage of 30 mg/kg). Hermorheology indexes were determined which include specific viscosity of whole blood, specific viscosity of plasma, erythrocyte sedimentation and hematokrit.

TABLE 9

The effect of Shengmaichenggu capsule on hermorheology index of rat acute blood stasis model ($x \pm s$)

| Group | Number of animal | Dosage/kg/day | Specific viscosity of whole blood | | Specific viscosity of plasma | Erythrocyte sedimentation | Hematokrit |
| | | | Lower shearviscosity coefficient | High shearviscosity coefficient | | | |
|---|---|---|---|---|---|---|---|
| Control | 10 | 20 ml distilled water | 18.83 ± 1.10 | 5.43 ± 0.30 | 1.87 ± 0.10 | 1.40 ± 1.43 | 42.60 ± 1.35 |
| blood stasis model | 7 | 20 ml distilled water | 28.78 ± 2.17*** | 6.44 ± 0.19*** | 1.82 ± 0.13 | 2.73 ± 0.50*** | 45.86 ± 3.85* |
| Tetramethylpyrazine phosphate | 11 | 90 mg | 20.87 ± 2.63### | 5.59 ± 0.40### | 1.95 ± 0.08 | 1.80 ± 0.27## | 43.55 ± 2.39 |
| Shengmaicenggu | 8 | 7.68 g | 21.70 ± 1.90### | 5.64 ± 0.26### | 1.97 ± 0.19 | 1.75 ± 0.21## | 43.38 ± 2.88 |
| Shengmaicenggu | 9 | 3.84 g | 21.88 ± 2.53### | 5.83 ± 0.37## | 1.99 ± 0.20# | 1.99 ± 0.24# | 43.67 ± 1.58 |
| Shengmaicenggu | 12 | 1.92 g | 24.07 ± 1.74### | 6.01 ± 0.33## | 2.05 ± 0.19## | 2.19 ± 0.45 | 45.75 ± 3.28 |

3. Results

The specific viscosity of whole blood, erythrocyte sedimentation and hematokrit in blood stasis model group increased significantly compared with those of normal control group, (p<0.05, p<0.01). The specific viscosity of whole blood and erythrocyte sedimentation in tetramethylpyrazine-treated group and Shengmaichenggu capsule-treated group decreased significantly compared with those of model group. The specific viscosity of plasma of Shengmaichenggu capsule-treated group at middle and lower dosage decreased significantly as compared with that of the model group (P<0.01 or P<0.05). The two experiments above-mentioned indicated that Shengmaichenggu capsule (Pulse-facilitation and bone-formation capsule) has the effect of promoting blood circulation and removing blood stasis.

EXPERIMENTAL EXAMPLE 8

The Analgesic Effect of the Capsule Made from the Leaves of *Cajanus cajan*

1. Experiment of Writhing Response on Mouse
(1) Experimental Materials
Medicaments: Shengmaicenggu capsule (Pulse-facilitation and bone-formation capsule); indometacin, supplied by Guangdong Shiqi pharmaceutical manufactory, lot number 950306; 0.6% acetic acid, lot number: 951025.

Animals: 42 NIH mice weighting 18–22 g each mouse, including male and female by half and half, supplied by the animal feedlot of the Health Department of Guangdong Province, Certificate number: 96A03.

(2) Experimental Method

Divided the mice into 5 groups randomly, i.e. control group (0.2 ml/10 g distilled water), indometacin-treated group (0.013 g/kg) and three Shengmaichenggu capsule-treated groups (dosages are shown in table 10). The mice were administered by gavage for 7 days. At the time of 60 minutes after the administration at the day 7, injected 0.6% acetic acid to abdominal cavity of the mice (0.2 ml/one mouse). Recorded the first time when the writhing response appeared caused by pain for each mouse, the number of the writhing response appeared in 10 minute and the analgesic percent. The results were analyzed statistically and shown in table 10.

TABLE 10

The analgesic effect of Shengmaichenggu capsule on mouse (writhing response) ($x \pm s$)

| Group | Number of animal | Dosage/kg/day | The First time when the writhing response appeared(s) | Number of writhing mice | Analgesic percent (%) |
|---|---|---|---|---|---|
| Control | 8 | 20 ml distilled water | 214.75 ± 47.74 | 8 | 0 |
| Indometacin | 8 | 0.013 g | 572.75 ± 182.13### | 2## | 75## |
| Shengmaichenggu | 8 | 10.24 g | 476.75 ± 150.43### | 3## | 62.5## |
| Shengmaichenggu | 9 | 5.12 g | 454.22 ± 128.17### | 3## | 62.5## |
| Shengmaichenggu | 9 | 2.56 g | 327.56 ± 118.25 | 4 | 50 |

Comparing with the control group, for the group marked with #P < 0.05, for group with ##P < 0.01, for group with ###P < 0.001

(3) Experimental Results

Comparing with the normal control group, the time when the writhing response first appeared postponed significantly in the indometacin-treated group and the Shengmaichenggu capsule-treated groups with higher and middle dosage (P<0.001). The number of writhing mice decreased (P<0.01) and the analgesic percents increased (P<0.01). The results indicated that Shengmaichenggu capsule has analgesic effect on mouse pain induced by acetic acid.

3. Hot-plate Test on Mouse (1) Experimental Materials

Medicaments: Shengmaichenggu capsule; indometacin, supplied by Guangdong Shiqi pharmaceutical manufactory, lot number: 950306.

Animal: 75 NIH female mice weighting 18–22 g each mouse, supplied by the animal feedlot of the Health Department of Guangdong Province, Certificate number: 96A03.

(2) Method

Adjusted the temperature of water bath box to 55° C.±1° C. I.C. Immersed one big beaker in the water bath and put mice into the beaker. Recorded the period from the time when animals were put into the beaker to that when animals licked feet due to pain, and defined the period as the threshold of pain of that mouse.

Screened out the mice whose threshold of pain were in the range of 5–30 seconds, and divided them randomly into 5 groups including control group, indometacin-treated group and three Shengmaichenggu capsule-treated groups (The dosage are shown in table 11). Administered medicaments to animals by gavage for continuous 7 days. Determined the threshold of pain at the time of 30 minutes and 60 minutes after the administration at day 7 respectively, and observed the changes in the threshold of pain after administration. Room temperature should be controlled in the range of 15–20° C.

(3) Results

TABLE 11

The analgesic effect of Shengmaichenggu capsule on mouse (hot-plate test) (x ± s)

| Group | Number of animal | Dosage/ kg/day | Threshold of pain before administration (S) | Threshold of pain at different time after administration (S) | |
|---|---|---|---|---|---|
| | | | | 30 min | 60 min |
| Control | 15 | 20 ml | 18.80 ± 4.77 | 16.93 ± 4.42 | 16.47 ± 4.69 |
| Indometacin | 14 | 0.013 g | 18.93 ± 5.41 | 28.07 ± 6.67### | 24.64 ± 6.49### |
| Shengmaichenggu | 15 | 10.24 g | 17.00 ± 4.583 | 21.27 ± 4.43 | 24.53 ± 6.12### |
| Shengmaichenggu | 15 | 5.12 g | 17.60 ± 4.92 | 24.67 ± 7.26## | 21.27 ± 4.04# |
| Shengmaichenggu | 15 | 2.56 g | 18.80 ± 4.14 | 20.20 ± 3.43 | 22.53 ± 6.82## |

Note: Comparing with the control group, for the group marked with #P < 0.05, for group with ##P < 0.01, for group with ###P < 0.001.

The experimental results are shown in table 11. It can be seen that the threshold of pain before administration has no significant difference among these groups. 30 minutes after administration, the threshold of pain of indometacin-treated group and Shengmaicenggu capsule-treated group at middle dosage increased significantly as compared with that of the control group (P<0.01 or P<0.001). 60 minutes after administration, the threshold of pain of indometacin-treated group and Shengmaichenggu capsule-treated group at higher, middle and lower dosage increased significantly as compared with that of the control group (P<0.05, P<0.01 或 P<0.001).

EXPERIMENTAL EXAMPLE 9

The Antiphlogistic and Antioncotic Effect of the Capsule Made from the Leaves of *Cajanus cajan*

1. Experiment of the Mouse Pinnal Inflammation Induced by Dimethylbenzene (1) Experimental Materials Medicament: Shengmaichenggu capsule;

Animals: 40 NIH mice weighting 18–22 g each mouse, supplied by the animal feedlot of the Health Department of Guangdong Province, Certificate number: 96A03.

(2) Method

Divided the mice into 5 groups randomly with 8 mice each, i.e. control group, indometacin-treated group and three Shengmaichenggu capsule-treated groups (dosages are shown in table 12). The mice were administered medicaments in different concentration by gavage. In the morning of day 7, 30 minutes after administration, pressed tampon soaked with dimethylbenzene on the left ear for about 5 seconds. Killed the mice after 15 seconds by decollation. Cut out the equal area at the same position from both ears of the mouse with perforator, and weighted with torsion balance. The swell degree is defined as the weight difference of subtracting the weight of the right ear from that of the left. Analyzed the data of swell degree of the control group and the treated groups statistically.

(3) Experimental Results

TABLE 12

The effect of Shengmaichenggu capsule on mouse pinnal inflammation caused by dimethylbenzene (x ± s)

| Group | Number of animal | Dosage/kg/day | Swell degree (mg) |
|---|---|---|---|
| Control | 8 | 20 ml distilled water | 0.8375 ± 0.3378 |
| Indometacin | 8 | 0.013 g | 0.5500 ± 0.258 |

TABLE 12-continued

The effect of Shengmaichenggu capsule on mouse pinnal inflammation caused by dimethylbenzene (x ± s)

| Group | Number of animal | Dosage/kg/day | Swell degree (mg) |
|---|---|---|---|
| Shengmaichenggu | 8 | 10.24 g | 0.3500 ± 0.1195## |
| Shengmaichenggu | 8 | 5.12 g | 0.8125 ± 0.5768 |
| Shengmaichenggu | 8 | 2.56 g | 0.4875 ± 0.2167# |

Note: Comparing with the control group, for the group marked with #P < 0.05, for group with ##P < 0.01

The experimental results are shown in table 12. It can be seen that the swell degree of Shengmaichenggu capsule-treated groups at higher and lower dosage decreased significantly as compared with that of the control group (P<0.05 或 P<0.01). The results indicate that Shengmaichenggu capsule can inhibit mouse pinnal inflammation caused by dimethylbenzene.

2. Test of Granuloma Induced by Tampon on Rat (1) Experimental Materials

Medicaments: Shengmaichenggu capsule; prednisone acetate, supplied by Xianju pharmaceutical Co. Ltd., Lot number: 950523.

Animals: 60 SD rats, body weight 150–200 g, supplied by the animal feedlot of the Health Department of Guangdong Province, Certificate number: 96A02.

(2) Method

The rats were divided into 5 groups randomly with 12 rats each group, i.e. control group, prednisone acetate-treated group and three Shengmaichenggu capsule-treated groups. An incision was made aseptically along the dorsimeson of a rat anesthetized by pentobarbital sodium and a sterilized tampon was imbedded into the incision and sewed up. The treated groups were administered by gavage 3 days before surgery until the day 7 after surgery. At the 8th day after surgery, the rats were killed by decollation. Avulsed out the tampon-caused granuloma tissue and dried it at 60–90° C. in a oven for 1 hour. Then weighted and subtracted the initial weight of tampon to get the net weight of granuloma tissue. Compared the granuloma weight among these groups and analyzed the results statistically.

(3) Results

TABLE 13

The effect of Shengmaichenggu capsule on tampon-induced granuloma of rat (x ± s)

| Group | Number of animal | Dosage/kg/day | Net weight of granuloma (mg) |
|---|---|---|---|
| Control | 12 | 20 ml distilled water | 64.29 ± 6.72 |
| Prednisone acetate | 12 | 25 mg | 33.45 ± 13.10### |
| Shengmaichenggu | 12 | 7.68 g | 56.24 ± 6.12# |
| Shengmaichenggu | 11 | 3.84 g | 56.41 ± 8.14# |
| Shengmaichenggu | 12 | 1.92 g | 52.37 ± 10.58## |

Note: Comparing with the control group, for the group marked with #P < 0.05, for the group with ##P < 0.01, for the group with ###P < 0.001

The experimental results are shown in table 13. It can be seen that the net weight of granuloma of prednisone acetate-treated group and the three Shengmaichenggu capsule-treated groups at every dosage decreased significantly as compared with that of the control group (P<0.05 or P<0.01). The results indicate that Shengmaichenggu capsule can inhibit granuloma.

EXPERIMENTAL EXAMPLE 10

Immunity Potentiating Effect of the Capsule Made from the Leaves of *Cajanus cajan*

1. Experiment of Nonspecific Immunological Functions

1). Experimental Materials

Medicaments: Shengmaichenggu capsule; levamisole, supplied by Guangdong Shiqi pharmaceutical manufactory, lot number: 950406; prednisone acetate, supplied by Xianju pharmaceutical Co. Ltd., Lot number: 950523.

Animals: 65 NIH mice weighting 18–22 g each mouse, including male and female by half and half, supplied by the animal feedlot of the Health Department of Guangdong Province, Certificate number: 96A03.

(2). Methods:

The mice were divided into 6 groups randomly, i.e. control group, modeled group, levamisole-treated group, and three Shengmaichenggu capsule-treated groups (dosages are shown in table 14). The modeled group, levamisole-treated group and three Shengmaichenggu capsule-treated groups were administered 0.3% prednisone acetate at a dosage of 0.2 ml/10 g body weight by gavage for continuous 7 days. Meanwhile administered different medicaments to these groups by gavage for continuous 20 days respectively. Administered distilled water to the control group by gavage in the same period. At the time of 30 minutes after administering on the day 20, injected Zhong-hua china ink into tail vein at a dosage of 0.01 ml/l10 g. At the 2th and 12th minute after injection, took 10 µl orbit blood and put into 3 ml 0.1% $Na_2CO_3$ solution and shook up. Detected optical density (OD) by colorimetric analysis in 722-grating photometer ($\lambda$=620). Calculated phagocytic index K and phagocytic index a according to the following equation:

$$K = \frac{\log OD1 - \log OD2}{T_1 - T_2} \quad X = \frac{W}{WLS}\sqrt[3]{K}$$

OD is the optical density of blood samples taken at different times, $T_2-T_1$ is the difference between the two sampling times, W is body weight, WLS is the total weight of liver and spleen, for the results were made by statistical analysis. The animals were killed by dislocating cervical vertebra. The liver and spleen were weighted respectively. Determined the weight of immune organs of every mouse according to the immune organ weighting method. Calculated the immune organ index and made a statistical analysis for the result.

(3) Experimental Results

TABLE 14

Effect of Shengmaichenggu capsule on the monocytophagous function of mouse

| Group | Number of animal | Dosage/kg/day | Phagocytic count K | Phagocytic activity α |
|---|---|---|---|---|
| Normal control | 10 | 20 ml distilled water | 0.0374 ± 0.0143 | 5.2784 ± 0.9169 |
| modeled | 12 | 20 ml distilled water | 0.0187 ± 0.00582* | 4.7002 ± 0.6249 |
| Levamisole | 12 | 0.04 g | 0.0273 ± 0.00852 | 5.1964 ± 0.7761 |
| Shengmaichenggu | 13 | 10.24 g | 0.0259 ± 0.0135 | 5.2355 ± 1.2854 |
| Shengmaichenggu | 9 | 5.12 g | 0.0216 ± 0.0112 | 4.7861 ± 1.1155 |
| Shengmaichenggu | 9 | 2.56 g | 0.0207 ± 0.0071 | 5.3286 ± 0.8556 |

Table 14 shows the effect of Shengmaichenggu capsule on the monocytophagous function of mouse. It can be seen that the count k of the model group decreases significantly as compared with that of the control group, α and K of the Shengmaichenggu capsule-treated groups at every dosages have an increasing trend.

TABLE 15

Effect of Shengmaichenggu capsule on the immune organs of mouse

| Group | Number of animal | Dosage/kg/day | Immune organ coefficient (mg/kg) Thymus (x ± s) | Spleen (x ± s) |
|---|---|---|---|---|
| Control | 11 | 20 ml | 2.772 ± 0.875 | 61.83 ± 1.908 |
| Model | 12 | 20 ml | 1.114 ± 0.268*** | 41.08 ± 1.081*** |
| Levamisole | 12 | 0.04 | 1.501 ± 0.334# | 52.82 ± 0.887### |
| Shengmaichenggu | 12 | 10.24 | 1.764 ± 0.271### | 54.75 ± 1.758### |
| Shengmaichenggu | 11 | 5.12 | 1.425 ± 0.133### | 47.56 ± 1.758### |
| Shengmaichenggu | 11 | 2.56 | 1.201 ± 0.207 | 40.11 ± 0.887 |

Table 15 shows the effect of Shengmaichenggu capsule on the immune organs of mouse. It can be seen that Shengmaichenggu capsule (Pulse-facilitation and bone-formation capsule) at both higher and middle dosage can improve the weight of thymus and spleen significantly (P<0.01 或 P<0.001). This indicates that Shengmaichenggu capsule (Pulse-facilitation and bone-formation capsule) can improve the mouse nonspecific immunological function and antagonize immunosuppression.

2. Experiment of the Content of Mouse Hemolysin
(1). Experimental Materials

Medicaments: Shengmaichenggu capsule; Levamisole, supplied by Guangdong Shiqi pharmaceutical manufactory, lot number: 950406; Prednisone acetate, supplied by Xianju pharmaceutical Co. Ltd., Lot number: 950523; 5% Suspension of chicken red blood cells in physiological saline; 10% Complement (Physiological saline: Mouse serum=3:2)

Animals: 60 NIH mice weighting 18–22 g each mouse, including male and female by half and half, supplied by the animal feedlot of the Health Department of Guangdong Province, Certificate number: 96A03.

(2) Experimental Method

The grouping and administering scheme was the same as that of the above-mentioned Experiment of nonspecific immunological functions. At the first day of administration, injected 5% suspension of chicken red blood cells to abdominal cavity of mice at a dosage of 0.2 ml/one mouse. Seven days after immunization, took blood from eyeball and centrifuged. The serum was diluted 100 times with physiological saline. 1 ml of the diluted serum was mixed with 0.5 ml of 5% suspension of chicken red blood cells and 0.5 ml of 10% complement. After incubation in an incubator at 37° C. for 30 minutes, the reaction was terminated by putting the mixture into a 0° C. refrigerator.

The formulated test solution was centrifuged. Took the supernatant and detected optical density (OD) by colorimetric analysis in 722-grating photometer ($\lambda$=620). Set up a control group free of serum and took the supernatant of the centrifuged test solution of this group as the "0" basis for colorimetric assay. Took "OD" as the index for quantifying the serum hemolysin and analysed the data statistically.

(3). Experimental Results

TABLE 16

Effect of Shengmaichenggu capsule on the hemolysin content of mouse immunised by chicken blood cells (x ± s)

| Group | Number of case | Dosage/kg/day | OD (Optical density) |
|---|---|---|---|
| Control | 10 | 20 ml distilled water | 0.9083 ± 0.1790 |
| Model | 10 | 20 ml distilled water | 0.5055 ± 0.1488*** |
| Levamisole | 10 | 0.04 g | 0.7370 ± 0.1444 |
| Shengmaichenggu | 10 | 10.24 g | 0.6820 ± 0.33802 |
| Shengmaichenggu | 10 | 5.12 g | 0.8180 ± 0.3441## |
| Shengmaichenggu | 10 | 2.56 g | 0.8110 ± 0.3072# |

From the experimental results shown in table 6, it can be seen that the "OD" values of the model group decrease significantly as compared with that of the control group (P<0.001). This indicates that prednisone acetate can reduce the hemolysin content of mouse immunized by chicken blood cells. The "OD" values of Shengmaichenggu capsule-treated groups at middle and lower dosages increase significantly as compared with that of the model group (P<0.05 or P<0.01). This indicates that Shengmaichenggu capsule can increase the hemolysin content of mouse immunized by chicken blood cells when it is immunosuppressed by prednisone acetate and improve the mouse humoral immunological function and antagonize immunosuppression.

3. Cellular Immunity Test (1). Experimental Materials

Medicaments: Shengmaichenggu capsule; Levamisole, supplied by Guangdong Shiqi pharmaceutical manufactory, lot number: 950406; PHA (Phytohaemagglutinin, supplied by Biology Department of Jinan University, Lot number: 960611; 5% Suspension of chicken red blood cells in physiological saline; 10% Complement (Physiological saline: Mouse serum=3:2).

Animals: 60 NIH mice weighting 18–22 g each mouse, including male and female by half and half, supplied by the animal feedlot of the Health Department of Guangdong Province, Certificate number: 96A03.

(2). Experimental Method

The mice were divided into 6 groups randomly, i.e. control group, model group levamisole-treated group, and three Shengmaichenggu capsule-treated groups at different dosages (dosages are shown in table 17). Administered by gavage once a day for continuous 7 days. After the last administration, all the animals were immunized by injecting 5% suspension of chicken red blood cells to abdominal cavity at a dosage of 0.2 ml/one mouse. Then the animals were injected PHA to abdominal cavity at a dosage of 0.025 ml/10 g for continuous 3 days. All groups except control group were administered prednisone acetate at a dosage of 3 g/kg body weight by gavage for continuous 7 days. At the time of 12 hours after last administration, the experiment was carried out according to the Experiment of the content of mouse hemolysin mentioned above in which chicken blood cells were used as immunogen.

(3) The Result of the Test

Example 11

The Clinical Research of the Combination Effect of the Leaves of *Cajanus Cajan(L.)* Millsp. and the Extract thereof on Bed Sore.

1. Medicaments

The leaves of *Cajanus Cajan(L.)* Millsp. and the extract thereof; Shengji Ointment composed of zinc oxide, borneol, massicot, phenol, vaselin, acidun boricum and the like, which was the experiential formulation for treating the wound infection for more than 30 years used by the arthrosteopedic surgery and the surgical department of the First Affiliated Hospital of Guangzhou University Of Traditional Chinese Medicine.

2. Standard (1) The standard of dividing the stages of bed sore: According to the standard of dividing and judging the stages of bed sore which was defined in the probative text book basic nursing for the national middle medicine schools.

The first stage is the florid stage of blood stasis: Temporary blood circulatory disorder (reactive blood stasis) appears when the local skin was pressed. The symptom is that the skin becomes red, swelling, ardent, and aching.

The second stage is the stage of inflammatory infiltration: The red and swelling part infiltrates outward, expands, and transformates. The color of skin becomes black and the blebs appears on the surface. The patient felt painful.

The third stage is the stage of the superficial ulcer: The blebs are disrupted, the local site is infected, the superficial tissue necroses, and the ulcer is formed.

The forth stage is the stage of necrotic ulcer: The necrotic tissue invaded the lower layer of cutis vera and muscal layer ligament becomes visible and there is more pus. The necrotic tissue is black, graveoleat and caducous. The infection expands toward peripheral and deep tissues, even to bones, which can seriously cause pyemia.

TABLE 17

The effect of Shengmaichenggu capsule on the transformation reaction of mice lymphocyte

| Groups | animals | Dosage/ kg/day | limphoblast (%) | transition state cells (%) | Transformation rate of lymphocyte (%) |
|---|---|---|---|---|---|
| Normal control | 10 | distilled water 20 ml | 0.2390 ± 0.04725 | 0.2890 ± 0.02726 | 0.5280 ± 0.03458 |
| Model | 10 | distilled water 20 ml | 0.2010 ± 0.03929 | 0.2320 ± 0.03736** | 0.4330 ± 0.03561*** |
| Levamisole | 10 | 0.04 g | 0.4310 ± 0.05043### | 0.3050 ± 0.04950### | 0.7370 ± 0.03234### |
| Shengmaichenggu capsule | 10 | 10.24 g | 0.3650 ± 0.1083### | 0.2740 ± 0.04766# | 0.6390 ± 0.07795### |
| Shengmaichenggu capsule | 10 | 5.12 g | 0.3350 ± 0.05297### | 0.2530 ± 0.03401# | 0.5870 ± 0.03561### |
| Shengmaichenggu capsule | 10 | 2.56 g | 0.4000 ± 0.06218### | 0.2750 ± 0.04720# | 0.6750 ± 0.03923### |

The result was shown in Tab 17, which suggested that the transition state cells and the formation rate of lymphocyte in the model group was reduced significantly as compared with that of the control group ($p<0.01$ or $p<0.001$), and there is a reductive trend for the limphoblast of the model group as compared with that of the control group; the limphoblast and the transformation rate of lymphocyte of the three Shengmaichenggu Capsule groups and the Levamisole group were increased significantly as compared with that of the model group ($p<0.001$). The transition state cells of the Shengmaichenggu Capsule groups at higher and lower dosage and the levamisole group were increased significantly as compared that of model group ($p<0.05$), which suggested that the Shengmaichenggu Capsule can enhance the cellular immunity function of the mice.

(2) The method standard for calculating bed sore: 1) Area: The area is calculated by the way of computing the area of the plane geometric graph. 2) Time index for bed sore healing: Time index for bed sore healing the area of bed sore x the course of bed sore)/days for bed sore healing.

(3) The standard of evaluating the effect: 1) healing time: days from the day of initial administration to the day when the wound is cured completely. 2) healing standard: The wound surface was covered by endepidemis, and the wound disappeared completely.

(4) The inclusion standard of cases: 1) Disease type: only the bed sore patients suffering from craniocerebral injury, lower extremities fracture and spinal column injury with paraplegia are included. 2) Site: Only the cases of sacrococcygeal bed sore are included. 3) inclusion standard for dividing the bed sore stages: Patients whose symptoms met the requirements of standard 1), 2) and beyond bed sore second period.
4) Age and sex: Patients who met the requirements of standard 1), 2) and 3) can be included in spite of their age and sex.
(5) The exclusion Standard of cases: The cases of infection of burn with ulcer or furunculous abscess and sacrococcygeal infections caused by tuberculosis and hemorrhoidal ulcer are excluded.
3. Therapeutic Method
(1) Cleaning the wound: Bed sore wound was cleaned according to its condition. After general disinfection, all the necrose and inactivate soft tissues and dead bones were eliminated until the staxis of soft tissues and the facies ossea occurred. Then the wound was washed with aquae hydrogenii dioxidi or Eusol and normal saline.
(2) Changing the dressings: The surface of the cleaned wound was covered with the Shengji Ointment or the leaves of *Cajanus Cajan(L.)* Millsp. and the extract thereof. Change the dressings once a day wherein the used drugs were removed and the new drugs were applied according to the general rules of changing the dressings. When there was new epidermis on the wound, the drugs were changed once every three to four days.
4. The General Condition of the Patients in the Two Groups
(1) The group of the leaves of *Cajanus Cajan(L.)* Millsp. and the Extract Thereof: 34 men and 16 women aged from 19 to 86. The maximum area of the bed sore was 19 cm×12 cm (Stage IV), the minimum was 2 cm×1 cm (Stage II) and the average was 17.5 cm$^2$.
(2) The Shengji Ointment group: 22 men and 17 women aged from 19 to 90. The maximum area of the bed sore was 8 cm×7 cm (Stage IV), the minimum was 2 cm×1 cm (Stage II) and the average area was 9.9 cm$^2$.
5. The Result:
(1) The Bed Sore Healing Time of the Two Groups was Contrasted As was showed in Tab. 18, the bed sore healing time of the group of the leaves of *Cajanus Cajan(L.)* Millsp. and the extract thereof was 14 days (p<0.01) less than that of the Shengji Ointment group. The difference was significant.

TABLE 18 the contrasted bed sore healing time between the two groups (x ± s)

| Groups | Cases | Healing days |
|---|---|---|
| Cajanus Cajan (L.) Millsp | 50 | 28.16 ± 16.72 |
| Shengji Ointment | 39 | 44.54 ± 30.49 |

(2) The Contrasted Bed Sore Healing Time (Days) in Different Stages

As was shown in Tab. 19, the difference of the healing time between the groups was not significant, which suggested that the curative effect of two groups was almost the same.

TABLE 19 contrasted healing time from the medium state to the stage when bed sore was cured between two groups (x ± s)

| groups | Cases of stage II | Cases of Stage III | Cases of Stage IV |
|---|---|---|---|
| Cajanus Cajan (L.) Millsp | 12.30 ± 8.02 (12) | 26.90 ± 12.37 (23) | 43.14 ± 14.06 (15) |
| Shengji Ointment group | 18.50 ± 7.2 (13) | 44.20 ± 16.41 (18) | 87.50 ± 30.41 (8) |
| | P < 0.05 | P < 0.001 | P < 0.01 |

(3) The Contrasted Bed Sore Healing Time Index

TABLE 20 the contrasted bed sore healing time index between the two groups (x ± s)

| groups | Total index | Stage II | Stage III | Stage IV |
|---|---|---|---|---|
| Cajanus Cajan (L.) Millsp | 1.47 ± 1.18 | 0.87 ± 0.34 | 1.21 ± 0.84 | 2.33 ± 1.57 |
| Shengji Ointment group | 0.74 ± 0.35 | 0.52 ± 0.16 | 0.71 ± 0.31 | 1.06 ± 0.52 |
| | P < 0.01 | P < 0.01 | P < 0.01 | P < 0.01 |

It is the more scientific and accurate way to evaluate the effect of drugs by calculating the healing time as a control. The larger the time index is, the more effective the drug is, and vice verse. The difference of the bed sore healing time index between the two groups was shown in Tab. 20 which suggested that the leaves of *Cajanus Cajan(L.)* Millsp. and the extract thereof had reliable and excellent effect on bed sore.

When the bone in the bed sore site is exposed in the clinic observation, administration of drugs made from *Cajanus Cajan(L.)* Millsp. and the extract thereof would make several small pannus appear on the exposed surface of the bone, which is then grown into granulation, and jointed into a flake together with the granulation which was grown from edge to the central, forming the new granulation tissue to cover the wound surface. However this phenomenon was not observed in the Shengii Ointment group, wherein the granulation tissue sprawled slowly from ambitus to the central and was hard to cover the bare bones, so it is necessary to chose other extracts for antibacterial effect. As indicated above, among cases using drugs made from leaves of *Cajanus Cajan(L.)* Millsp. and the extract thereof, the granulation tissue on bed sore wound surface formed faster and covered wound surface more quickly while wound secretion was relatively less. The leaves of *Cajanus Cajan(L.)* Millsp. and the extract thereof was also confirmed to have better antibacterial effect on *staphylococcus aureus* by in vitro antibacterial test, which was equal to that of gentamicin (plant paper test). And the animal test also proved its antibacterial effect on acute, subacute and chronic inflammation model. The adverse effect of the drug was never appeared during the clinical use and the patients were response well.

EXAMPLE 12

The Clinical Research of the Effect of the Leaves of *Cajanus Cajan(L.)* Millsp and the Extract thereof on the Infected Wound Caused by Open Fracture 1. Clinical Information 18 cases were chosen aged from 14 to 70, wherein 6 cases suffered from wound, 7 cases experienced immobilization surgery after being wounded, 3 cases experienced amputation, and 2 cases suffered from gangrene dismemberment. Among them there were 8 cases with fracture at the position of lower 113 of the tibia and fibula, 2 cases with fracture at the upper ⅓ of the tibia and fibula, and 2 cases with fracture at the lower ⅓ of the femora.

2. Therapeutic Method

Only the drugs made from leaves of *Cajanus Cajan(L.)* Millsp. and the extract thereof were used to be spread on the surface of the wounded site for all the cases. The drug has a concentration of 1:2 (i.e. the aqueous solution with a concentration of 1:2 prepared by the leaves of *Cajanus Cajan(L.)* Millsp. and the extract thereof and the distilled water for injection), PH of 5.3, and was packed in bottles after disinfection. The operation should meet asepsis requirement when changing used drugs with new drugs. The wound surface was sopped with a piece of carbasus which had been soaked in the drug solution before use, and covered and bandaged with vaseline carbasus and sterilized dressing. When the wound infection was obvious, the administration was carried out once a day; when the granulation tissue appeared and the exudatum was reduced, the administration was carried out twice a day; when wound surface was covered by new granulation tissue completely, it was changed to use the mixed solution of gentamycin and normal saline to perform hydropathic compress. After three days, free skin grafting was operated with pieces of medium pachydema. Three days after operation, the Chinese herbs were continued to used for performing hydropathic compress until the wound was cured.

3. Observation Items:

In order to observe the change of the wound surface we took the dynamic color image during different time before and after the administration. The germiculture and the drug sensitivity test were carried out for the secretion on the wound surface; The occurring time, developing rules and the growth condition of epithelial granulation tissue, the granulation islands, and the wound surface's healing time were observed. The histological inspection of granulation on the wounded surface was also observed.

4. The Result

In the clinical test, 15 cases' infection was controlled during 3 days, other 3 cases' infection would be controlled after extirpating dead bones caused by its long time infection with bones infection and bones necrosis. The exudatum was reduced quickly after the administration, and the granulation tissue occurred 2 to 5 days after the administration. It was scarlet and easy to bleed if touched. The granulation tissue could cover the wound surface when it extended to the edge skin of the wound.

5. Conclusion

The leaves of *Cajanus Cajan(L.)* Millsp. and the extract thereof had better anti-infective effect on clinical infected wound surface and could enhance the growth of the granulation tissue. It also increased the blood supply of the wound surface and accelerated the agglutination of the wound. Especially, it could make granulation tissue which was called bone granulation islands grow on the bone which was exposed to the wound surface

EXAMPLE 13

The Effect of the Leaves of *Cajanus Cajan(L.)* Millsp. and the Extract Thereof on the Healing of the Open Infected Wound Surface 1. The Effect of Leaves of *Cajanus Cajan(L.)* Millsp. and the Extract thereof on Agglutination of Open Infected Wound Surface (1) Experiment Materials The solution of the leaves of *Cajanus Cajan(L.)* Millsp. and the extract thereof with the concentration of 1:2 (i.e. the aqueous solution with the concentration of 1:2 prepared by the leaves of *Cajanus Cajan(L.)* Millsp. and the extract thereof and the distilled water for injection), PH 5.3, which was packed in bottles after disinfection.

The model of wound infection on the rabbits' two fore-legs was established as follow: 19 healthy rabbits with the body weight of 2–2.8 kg were selected no matter what sexuality they were. The animal were divided into three groups to establish the model of the two fore-legs' open wound surface, then inoculated with bacterium. It was proved by pro-test that the infection of wound surface approached to the peak at 72 hours later after inoculation.

(2) Drug Application

The drug was applied on the surface of the infection, wherein the drug was applied twice a day for the first week, once a day from the second week to the time when the wound surface was substantially cured, and once every there days when the wound surface was substantially cured or cured completely. It should be ensured the applied dosage was the same. Furacilin was used as the control.

(3) The Method for Observing and Evaluating Indicators

The determination was carried out once every three days by describing the edge of the wound surface during the time when the wound surface was formed, before and after the administration. The healing time of the wound surface was determined by statistically processing the curve graph for the area of the wound surface versus the time and the value of the area for every group at every time; and checking the wound epidermis and the granulation tissue and scar tissue both visually and by optical microscope (4) The Result of the Test The renovating effect of the leaves of *Cajanus Cajan(L.)* Millsp. and the extract thereof on the wound surface was superior to that of control group after 9 days of administration. The eventual healing time of wound was about one week ahead of that of the control, which showed a significant difference ($p<0.05$).

(5) Conclusion

The leaves of *Cajanus Cajan(L.)* Millsp. and the extract thereof have the effects of enhancing the growth of granulation tissue on the wound surface, increasing the blood supply of the wound surface, accelerating the agglutination of the wound, decreasing the formation of scar and improving the quality of agglutination of wound.

2. The Anti-infection Effect of Leaves of *Cajanus Cajan(L.)* Millsp. and Extract thereof on Open Infected Surface of Wound (1) Experimental Material The solution of the leaves of *Cajanus Cajan(L.)* Millsp. and the extract thereof with the concentration of 1:2 (i.e. the aqueous solution with the concentration of 1:2 prepared by the leaves of *Cajanus Cajan(L.)* Millsp. and the extract thereof and the distilled water for injection), PH 5.3, which was packed in bottles after disinfection.

The model of wound infection on the rabbits' two fore-legs was established as follow: 6 healthy rabbits with the body weight of 2.5–3 kg were selected no matter what sexuality they were. The animal were divided into three groups to establish the model of the two fore-legs' open wound surface, then inoculated with bacterium and concentration of bacterium was increased to 9 hundred million bacteria/ml. It was proved by pro-test that the infection of wound surface approached the peak at 36 hours after inoculation.

(2) Application of Medicament

The above medicament was used externally when the infection of wound surface approached the peak, administrated twice per day (8 AM and 4 PM each), normal saline used as control.

(3) Observation Item

The dynamic color images of the surface of wound was taken before administration and at the different time of administrating. The infectious change of the surface of wound was observed; The range of aula ring and color variation around the surface of wound was observed, and the congestion state of the surface of wound was found out. The degree of peripheral tumid and the amount change of secretion on the surface of wound were observed so that the exudation state of the surface of wound can be known.

(4) Experimental Result

The renovation effect of Leaves of *Cajanus Cajan(L.)* Millsp. and the extract thereof on surface of wound was superior to that of control group after 9 days of administration. The final healing time was about one week ahead of that of the control group, which showed a significant difference ($p<0.05$).

(5) Experimental Conclusion

The Leaves of *Cajanus Cajan(L.)* Millsp. and the extract thereof have good effect of anti-infection on infected surface of wound which was indicated by that the surface of wound and inflammatory response regressed quickly, especially the exudation of the surface of wound reduced soon and the wound became clean after administration. This showed that the medicament possess the favorable effect of anti-inflammatory exudation.

EXPERIMENTAL EXAMPLE 14

The Curative Effect Observation of Leaves of *Cajanus Cajan(L.)* Millsp. and the Extract thereof Applying to 564 Cases with Infected Surface Wound.

1. Clinical Information

Leaves of *Cajanus Cajan(L.)* Millsp. and the extract thereof was applied clinically to the diseases such as traumatic surface, infected surface of wound, burn infection, bedsore etc. in the past more than 6 years, and the curative effect of 564 cases was observed.

2. Experimental Method

The secretion of infected surface of wound was cultured for bacteria. Usually *Bacillus proteus pyocyaneus, Bacillus coli, Staphylococcus albus, staphylococcus aureus* Rosenbach, few *Bacillus subtilis, Bacillus aerogenes* are often applied. After the drugs made from Leaves of *Cajanus Cajan(L)* Millsp. and the extract thereof were external applied on the infected surface of wound topically for 3–5 days, the secretion and odor reduced, putrilaginous tissue was dispelled fast, florid granulation surface of wound was appeared gradually. After the drugs of the invention was applied to the larger surface of wound for 2 weeks, the skin grafting can be conducted basically; skeletons were exposed and granulation insulas were seen grown with Haversian system after administration, covered the surface of bone gradually; muscle tendon parts must be moistened by applying drug liquid in order to avoid necrosing.

3. Conventional Preparation (1) The fresh leaves of *Cajanus Cajan(L.)* Millsp. were cleaned and soaked in 1% bromo-geramine for 20 minutes, air dried, then pounded, spread on the surface of the wound directly, or one layer gauze was spread on the surface of the wound, then the drug was spread on the gauze, and the drug liquid could permeate the gauze and act on the surface of the wound, and afterwards the wound was bundled with dressing at outside surface. (2) The surface of the wound was wetted with 200% inspissant of leaves of *Cajanus Cajan(L.)* Millsp. and the extract thereof, the former method of (1) had better curative effect when both were compared. (3) The leaves of *Cajanus Cajan(L.)* Millsp. were boiled in water to get liquid, then the surface of the wound was soaked with the liquid for about 30 minutes.

4. Results (1) The clinical effects of removing necrotic tissue and promoting tissue regeneration were observed for the leaves of *Cajanus Cajan(L)* Millsp. and the extract thereof when they were applied on the infected surface of wound. Generally when 3–5 days external application, or 1 to 2 weeks external application for the larger surface of wound after administration, the secretion reduced markedly, odor disappeared quickly and the curative effect is satisfied relatively.

(2) After the leaves of *Cajanus Cajan(L.)* Millsp. and the extract thereof were externally applied, the grown granulation became florid without little edema. The grown granulation with the drugs of the invention was more florid and vigorous than that grown after Eusol solutions 1% rotten sodium phytate solutions normal saline etc. were externally applied. The effect of fresh leaves is better than the boiled liquid of the leaves. So it was considered that leaves of *Cajanus Cajan(L.)* Millsp. and the extract thereof not only have the bactericidal and bacteriostatic effect, but also have the anti-inflammatory effect, probably they also have a nutrient factor of promoting cell growth. When the infected surface of wound after punctual skin grafting on burn wound was wetted with the solution made from leaves of *Cajanus Cajan(L.)* Millsp. and the extract thereof, not only the infection could be controlled, but also it could be observed that the grown rate of the grafted skin is faster than that of the grafted skin where the drug of the invention was not applied.

(3) Usually it was relative difficult to treat the infection under the scab of burn wound, or the infection resulted from grafting skin, especially the infection of *Bacillus aeruginosus* after grafting skin. But when the 200% solution made of the leaves of *Cajanus Cajan(L.)* Millsp. and the extract thereof were used to moistened the infected wound which was exposed half, the effect was better than that of wet dressing with antibiotics. There is no worry of resistance resulted from antibiotic.

INDUSTRIAL APPLICABILITY

The leaves of *Cajanus Cajan(L.)* Millsp. is a species legume vivacious plant planted in south subtropics, so its source is abundant, and the technology of the invention is easy to be popularized. The inventive method of preparing the extract of the leaves of *Cajanus Cajan(L.)* Millsp. is handy and easy-to-use. It was proved by animal experiment and clinical observation that the leaves of *Cajanus Cajan(L.)* Millsp. and the extract thereof have obvious curative effect on ischemic necrosis of femur head, osteoporosis, ameliorateing hemorheological index, the anti-inflammatory and analgesic, reinforcing immunological function, coronary heart disease angina, fracture, cerebral infarction, bedsore, infected surface of wound and the infected surface of wound of open fracture etc., and have powerful pharmacological effect. The Leaves of *Cajanus Cajan(L.)* Millsp. and the extract thereof as active component could be formulated into various clinical preparation such as tablet, pill, powder, capsule, oral liquid etc. by conventional preparation technique, and have favorable industrial applicability.

What is claimed is:

1. A method of treating angina of coronary heart disease, comprising administering a subject in need thereof leaves of *Cajanus cajan(L.)* Millsp. or an extract thereof.

2. The method treating cerebral infarction, comprising administering a subject in need thereof leaves of *Cajanus cajan(L.)* Millsp. or an extract thereof.

* * * * *